(12) United States Patent
Gottlund

(10) Patent No.: US 7,517,537 B1
(45) Date of Patent: Apr. 14, 2009

(54) PROCESS FOR DECONTAMINATING A FLUID

(75) Inventor: Kathy L. Gottlund, Kutztown, PA (US)

(73) Assignee: Puritek Inc., Short Hills, NJ (US)

( * ) Notice: Subject to any disclaimer, the term of this patent is extended or adjusted under 35 U.S.C. 154(b) by 0 days.

(21) Appl. No.: 12/001,105

(22) Filed: Dec. 10, 2007

Related U.S. Application Data

(63) Continuation of application No. 10/441,002, filed on May 20, 2003, now abandoned, which is a continuation-in-part of application No. 10/051,685, filed on Jan. 22, 2002, now Pat. No. 6,565,866.

(51) Int. Cl.
*A61K 9/70* (2006.01)
*A61K 9/00* (2006.01)

(52) U.S. Cl. .................. 424/443; 424/400; 424/404
(58) Field of Classification Search ............. 424/400, 424/443, 404
See application file for complete search history.

(56) References Cited

U.S. PATENT DOCUMENTS 4,888,118 A * 12/1989 Barnes et al. ............... 210/668
5,669,937 A * 9/1997 McBride et al. ................ 8/137

\* cited by examiner

*Primary Examiner*—Taylor Victor Oh
(74) *Attorney, Agent, or Firm*—Law Firm of Walter D. Ames

(57) ABSTRACT

A process for decontaminating water, comprising contacting the water with iodine, contacting the solution with a nylon polymer selected from the group consisting of nylon-6, nylon-4,6 and nylon-6,6, and then separating the so-formed iodophor from the solution.

12 Claims, No Drawings

PROCESS FOR DECONTAMINATING A FLUID

This application is a continuation of application Ser. No. 10/441,002, filed May 20, 2003 and to be abandoned, and a continuation-in-part of application Ser. No. 10/051,685, filed Jan. 22, 2002 and now U.S. Pat. No. 6,505,866.

FIELD OF THE INVENTION

The present invention relates generally to a process for decontaminating a fluid. More specifically it refers to such a process in which iodine is utilized as the means for decontaminating the fluid and, after the iodine has had its desired effect, an agent is introduced into the fluid to sequester the iodine so that it can be efficaciously removed from the fluid.

BACKGROUND OF THE INVENTION

It is well known that iodine is one of the best decontaminating agents known. It is readily available, either as elemental iodine or more commonly in the form of potassium iodide, and has proved effective against Gram Positive and Gram Negative bacteria, fungi, spores and viruses. Thus, the addition of iodine or a form thereof from which iodine will be released is known as an effective way to decontaminate fluids, which term includes both liquids and gases.

However, while iodine is an essential element in human diet, its presence in a fluid, particularly in water in quantities sufficient to kill bacteria and viruses. will be offensive and render the water undrinkable. Iodine has an unpleasant odor and tends to impart a yellowish brown color to water and other fluids. So, after iodine has been in contact with a fluid to be decontaminated and has accomplished its purpose as a bactericide, the problem remains as to how to remove the iodine from the fluid, in the case of water, so that the water can be rendered potable. While some iodine is necessary in the human diet, excess iodine irritates animal tissue and can be poisonous.

It has thus become necessary to find a simple way to remove iodine from a solution or fluid after the iodine has accomplished its decontaminating function, and the use of a nylon polymer to perform this function has been recognized. That prior art with which the present inventor is familiar is U.S. Pat. No. 4,888,118 to Carl E. and Arthur C. Barnes. Such patent discloses that iodine may be used for the treatment of water, and that the iodine may thereafter be removed from the water/iodine solution by complexing it with nylon-4. Nevertheless, in what might appear to be a contradiction, Barnes also discloses that iodine may be introduced into impure water by the use of a nylon-4/iodine complex, i.e., an iodophor., and Barnes cites to Canadian Patent No. 1,119,748 for the disclosure of the use of a nylon-4/iodine complex as the source of iodine to destroy microorganisms and make the water potable. Indeed, it is clear from the Barnes's disclosure that the use of a nylon-4 iodophor is their preferred manner of adding iodine to contaminated water.

As Barnes explains, and as I have confirmed, the use of nylon-4 to sequester iodine, as opposed to utilizing it to supply iodine to a solution, presents a problem. When the iodine concentration is very low compared to a considerable excess of nylon-4 polymer, the equilibrium will swing in favor of the iodophor complex. However, when the system is more heavily loaded with iodine, e.g., perhaps 5% iodine, an equilibrium will be established in which a substantial quantity of iodine is left in the water. This is a situation that is highly undesirable, because the water treated with the nylon-4 polymer will have a taste and color from the iodine, making it undesirable for drinking purposes. The only solution would be to use large quantities of nylon-4 polymer, an event that could make the entire procedure impractical.

It is, therefore, a primary object of the present invention to provide a method of utilizing a polymer to sequester decontaminating iodine from a fluid, usually water, in which the polymer complexes with the iodine and the complex has such a slow release of iodine that it and its complexed iodine can be removed from the fluid before the substantial release of iodine from the complex.

As a solution to the problems present through the use of a nylon-4 iodophor to complex iodine, it has been determined that the iodine in the solution should have such a slow release of iodine that equilibrium between the polymer and iodine, at which equilibrium substantial quantities of iodine may be present in the solution, will not be released until well after the iodophor complex has been removed from the solution, thereby preventing the release of iodine from the complex to the fluid, as is the case with the nylon-4 iodophor disclosed in the Barnes patent.

SUMMARY OF THE INVENTION

The present invention is directed basically toward a process for decontaminating a fluid such as water by contacting the fluid with iodine to kill contaminants in the fluid, then contacting the iodine containing fluid with a nylon polymer selected from the group consisting of nylon-6, nylon-6,6, and nylon-4,6 and combinations thereof. The iodine may be specifically added to the fluid in order to remove harmful bacteria and viruses. However, the iodine in the fluid may be a contaminant thereto, e.g., coolant water from a nuclear power plant. The polymer-iodine complexes, referred to as iodophors, that have been formed are thereafter removed from the fluid. If the fluid is a liquid, e.g., water, such removal can be effectively accomplished by decantation or filtration.

It is an important aspect of my process that the iodophor be removed from the fluid within such time as will enable the polymer and iodine to have formed an iodophor complex with as much of the iodine present as possible, but as soon as practical thereafter. In this manner the iodophor will have been removed prior to the substantial release of iodine from the complex. Indeed, if the iodophor is permitted to remain in the fluid over an extended period of time, an equilibrium will be reached between the complex and its components, and it is desirable that the iodophor be removed from the fluid or solution prior to that equilibrium point.

As subsidiary facets of my invention, the nylon polymer added to the solution can be in the form of fibers or pellets. For some purposes the iodine may be in the form of radioactive iodine.

These and other objects, features and advantages of the present invention will become more apparent when considered in connection with the following description of preferred embodiments of my invention as described more fully hereinafter.

DESCRIPTION OF PREFERRED EMBODIMENTS

I have found that while nylon-4 possesses certain properties that make it desirable for use as a sequestering or scavenging agent, it also has properties that, as a practical matter, make it a very poor scavenging agent. Thus, it is known that nylon-4 is produced by the ring opening polymerization of pyrrolidone. The so-formed polypyrrolidone contains repeating units of four carbon atoms, oriented in the so-called "head (NH) to tail (C=O)" configuration.

With respect to uptake of iodine to form an iodophor complex, nylon-4 most readily takes up iodine from a solution to form an iodophor. This expectation is due to the close proximity of the carbonyl and/or amine radicals of the repeating groups of the polymer chain. However, in its application to a process for sequestering iodine from a solution, the nylon-4 iodophor also has the highly undesirable property of releasing iodine from the complex. Such release is, indeed, too rapid to be successfully used in a dynamic environment where the desired result is the removal or all or substantially all of the iodine from the environment.

Experiments were performed using nylon-4, nylon-4,6, nylon-6, and nylon -6,6 fibers to sequester iodine from solutions, with different initial concentrations of iodine bound. The results are graphically illustrated in Exhibit A.

As shown in Exhibit A, the rate of release of iodine from a nylon-iodine iodophor was plotted for four different iodophors: those formed by the complexing of iodine with nylon-4, nylon-4.6, nylon-6, and nylon-6,6. The percent of iodine released from each iodophor was calculated over a period of 0 to 60 minutes, with absorbance being measured at 490 nm. The nylon iodophors with different concentrations of iodine bound were exposed to fresh tap water and the iodine released over a 60 minute period was measured.

It will be seen from the graph of Exhibit A that the nylon-4 iodophor, with only 11% (wt/wt) iodine bound, rapidly released iodine into solution, coming to an equilibrium at the 11 minute time point. In contrast, the nylon-4,6 iodophor, with more than twice the amount of iodine bound, 30% (wt/wt), released a substantially lesser quantity of bound iodine than did the nylon-4 iodophor, even at its equilibrium point. Both the nylon-6 and nylon-6,6 iodophors continued to release iodine slowly, possibly reaching an equilibrium near the 60-minute time point.

The same tests were repeated using nylon polymer in the form of pellets rather than fibers. The results of those experiments were graphed as Exhibit B, in which time in minutes of exposure to tap water was plotted against consequent iodine release, for the four different nylon iodophors.

As will be seen from the Exhibit B graph, nylon-4, with only 2.7% of iodine bound (wt/wt), rapidly released more total iodine into solution than any of the other nylon iodophors, although those other nylon iodophors started the tests with a greater percent of iodine bound. Those percentages of iodine bound were: nylon-4,6-4.4%, nylon-6-3.0%, and nylon-6,6-3.6%.

It has thus been determined that when an iodophor is to be utilized to scavenge a solution for iodine, and then to remove that iodophor from the fluid or solution, nylon-4 iodophors are markedly inferior to those formed from nylon-4,6, 6, and 6,6. The properties of the last three nylon iodophors that are important in such a process are that the sequestration process is gradual rather than immediate, thereby giving the iodine more time to decontaminate the solution. Even more important is the fact that with those three nylon polymer iodophors the release is far more gradual, thereby enabling one to calculate the time during which the polymer should remain in contact with the iodine, with possible agitation, before the thus formed iodophor should be removed from the solution. In this manner the nylon-4,6, 6, and 6,6 iodophor complexes can be removed from the solution at the proper time prior to equilibrium so that a maximum percentage of iodine will have been sequestered.

It will be apparent that certain alterations and modifications of the preferred embodiments of my invention will be obvious to those of skill in this art. As to all such obvious changes, it is desired that they be included within the purview of my invention, which is to be limited only by the scope, including equivalents, of the following, appended claims.

I claim:

1. A process for decontaminating a fluid, comprising the steps of contacting said fluid with iodine to kill contaminants in the fluid, contacting the iodine containing fluid with a nylon polymer selected from the group consisting of nylon-4,6, nylon-6 and nylon-6,6 and combinations thereof to form an iodophor between said nylon polymer and said iodine in said fluid, and thereafter separating said iodophor from said fluid by decanting or filtration prior to the release of undesirable quantities of iodine from said iodophor.

2. A process as claimed in claim 1, in which said iodophor is separated from said fluid by decantation.

3. A process as claimed in claim 1, in which said iodophor is separated from said fluid by filtration.

4. A process as claimed in claim 1, in which said nylon polymer is in the form of fibers.

5. A process as claimed in claim 1, in which said nylon polymer is in the form of pellets.

6. A process as claimed in claim 1, in which said iodine and said nylon polymer are added to said fluid sequentially, with said iodine being added first and said polymer being added within one minute after the addition of said iodine.

7. A process as claimed in claim 1, in which said nylon polymer is nylon-6.

8. A process as claimed in claim 1, in which said iodine is radioactive iodine.

9. A process for removing contaminants from a liquid by the use of iodine, comprising adding to a contaminated liquid a source of iodine in such concentration and quantity as will deactivate said contaminants, then adding to said fluid a nylon polymer selected from the group consisting of nylon-4,6, nylon-6 and nylon-6,6 and combinations thereof, permitting said liquid to remain in contact with said polymer to form an iodophor between said polymer and the iodine in said liquid, and thereafter separating said iodophor from said liquid prior to the formation of an equilibrium between said iodophor, on the one hand, and the iodine and nylon polymer, on the other.

10. A process as claimed in claim 9, in which said nylon polymer is selected from the group consisting of nylon-4,6 and nylon-6, and said polymer is in the form of fibers.

11. A process as claimed in claim 9, in which said liquid is agitated at least sporadically during said time the liquid remains in contact with the polymer.

12. A process as claimed in claim 11, in which said liquid is contaminated water.

* * * * *